United States Patent [19]
Hayashida et al.

[11] Patent Number: 5,188,922
[45] Date of Patent: Feb. 23, 1993

[54] OPTICAL RECORDING MEDIUM

[75] Inventors: Shigeru Hayashida; Seiji Tai, both of Hitachi, Japan

[73] Assignees: Hitachi Chemical Company, Ltd.; Hitachi, Ltd., both of Tokyo, Japan

[21] Appl. No.: 703,056

[22] Filed: May 17, 1991

Related U.S. Application Data

[63] Continuation of Ser. No. 596,427, Oct. 11, 1990, abandoned, which is a continuation of Ser. No. 325,963, Mar. 20, 1989, abandoned, which is a continuation of Ser. No. 76,483, Jul. 22, 1987, abandoned.

[30] Foreign Application Priority Data

Jul. 23, 1986 [JP] Japan .................. 61-173394

[51] Int. Cl.$^5$ ................. G03C 1/72; G03F 7/26
[52] U.S. Cl. .................. 430/270; 430/495; 430/945
[58] Field of Search .................. 430/270, 495, 945

[56] References Cited

U.S. PATENT DOCUMENTS

| | | | |
|---|---|---|---|
| 4,131,609 | 12/1978 | Wynne et al. | 260/314.5 |
| 4,492,750 | 1/1985 | Law et al. | 430/494 |
| 4,626,496 | 12/1986 | Sato | 430/270 |
| 4,719,661 | 1/1988 | Hirox et al. | 369/109 |
| 4,725,525 | 2/1988 | Kenny et al. | 430/270 |

FOREIGN PATENT DOCUMENTS 0191970 8/1986 European Pat. Off. .

OTHER PUBLICATIONS

Journal of the American Chemical Society, vol. 106, No. 24, Nov. 1, 1984, Gaston, Pa. US; pp. 7404-7410; B. L. Wheeler: "A Silicon Phthalocyanine and a Silicone Naphthalocyanine: Synthesis, Electrochemistry, and Electrogenerated Chemiluminiscence".

Primary Examiner—Charles L. Bowers, Jr.
Assistant Examiner—Thorl Chea
Attorney, Agent, or Firm—Antonelli, Terry, Stout & Kraus

[57] ABSTRACT

The present invention relates to an optical recording medium laminated having on a substrate a recording layer comprising an organic thin film containing a silicon naphthalocyanine compound represented by the following general formula (I):

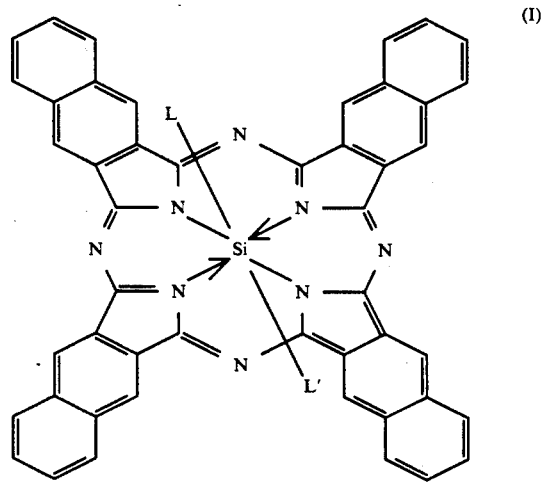

wherein L and L' each represents a group capable of linking to silicon.

2 Claims, 12 Drawing Sheets

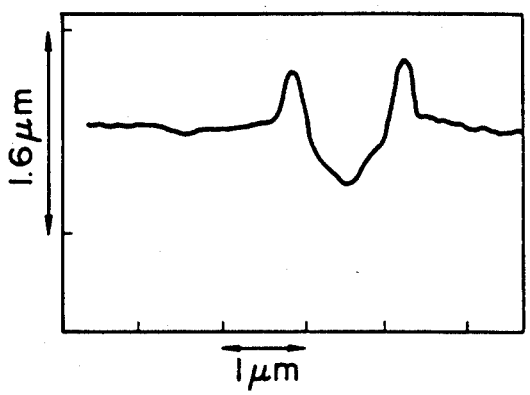
F I G. 2
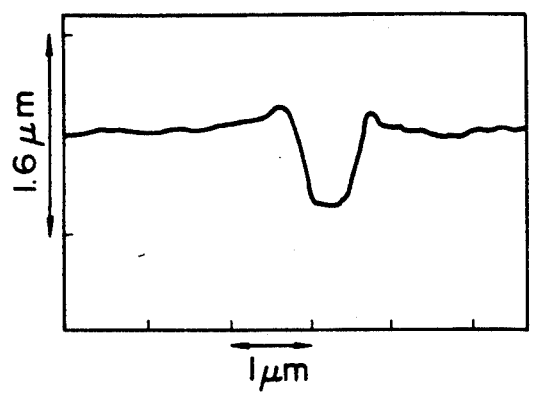
F I G. 4
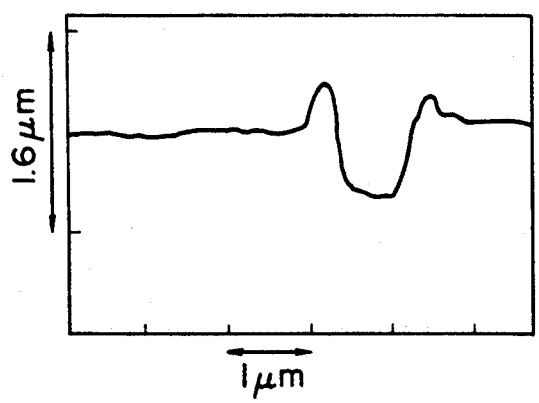
F I G. 3
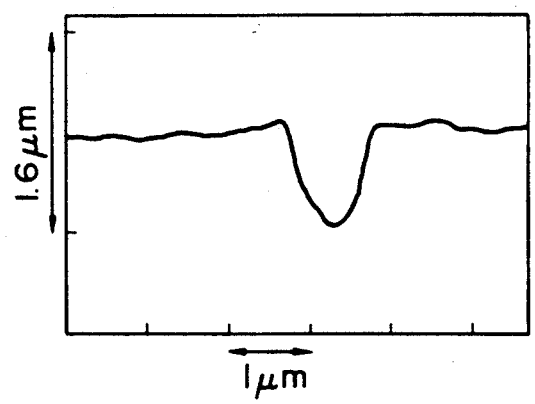
F I G. 5

FIG. II

OPTICAL RECORDING MEDIUM

This application is a continuation of application Ser. No. 596,427, filed Oct. 11, 1990 now abandoned, which is a continuation of application Ser. No. 325,963, filed Mar. 20, 1989, now abandoned which is a continuation of application Ser. No. 076,483, now abandoned filed Jul. 22, 1987 (now abandoned).

DETAILED DESCRIPTION OF THE INVENTION

1. Field of the Invention

The present invention relates to an optical recording medium, and more particularly to an optical recording medium which enables to write in or read out informations by the use of a diode laser having an absorption in the near infrared region.

2. Prior Art

Owing to the outstanding progress in the diode lasers in the recent years, small-sized stable laser oscillators are available today, and they have become used as light source of various recording apparatuses.

As its result, recording apparatuses using diode laser as their light source require a recording medium having absorption in the near infrared region Recording media having absorption in the relatively short wavelength region are unsuitable for this purpose.

As recording medium having absorption in the near infrared region, those having metallic or semimetallic (Te, Rh, Bi, etc.) thin film have been known hitherto. Thus, the thin film is perforated by laser beam irradiation and the change in reflectivity or absorptivity at the resulting hole is utilized for recording informations (Japanese Patent Application Kokai (Laid-Open) No. 264,293/85). Further, as recording materials made of organic compound, fluorescein, Brilliant Green, Disperse Red 11 (Japanese Patent Application Kokai (Laid-Open) No. 161,690/80) and the like are known. Further, as recording material having absorption in the near infrared region, naphthalocyanine compounds having $C_4$–$C_8$ alkyl substituent to the naphthalene ring are disclosed in U.S. Pat. No. 4,492,750.

PROBLEM TO BE SOLVED BY THE INVENTION

However, inorganic recording materials such as Te, Rh, Bi and the like are said to be disadvantageous in that their sensitivity is low and they are toxic. Organic dyes such as fluorescein, Brilliant Green, Disperse Red 11 and the like are disadvantageous in that writable light is limited to the lights having a wavelength of visible region. The alkyl-substituted naphthalocyanine compounds disclosed in U.S. Pat. No. 4,492,750 are disadvantageous in that they are thermally instable and incapable of forming thin film due to decomposition under the conditions of vacuum vapor deposition.

The present invention was invented in view of the above-mentioned state of things. Thus, the object of the invention consists in providing a novel recording medium which has a high sensitivity to the lights of near infrared region, has no toxicity, and can form a uniform thin film by the vacuum vapor deposition method.

After many studies, the present inventors have succeeded in inventing such a recording medium.

BRIEF DESCRIPTION OF THE DRAWINGS

FIGS. 2 through 5 illustrate the sectional shapes recording materials using bis(trihexylsiloxy)-silicon naphthalocyanine (He-NC, Example 2), bis(tributylsiloxy)-silicon naphthalocyanine (Bu-NC, Example 3), bis(tripropylsiloxy)-silicon naphthalocyanine (Pr-NC, Example 4) and bis(triethylsiloxy)-silicon naphthalocyanine (Et-NC, Example 5), respectively, measured after making record by irradiation of diode laser.

MEANS FOR SOLUTION OF THE PROBLEM

Figure 1:
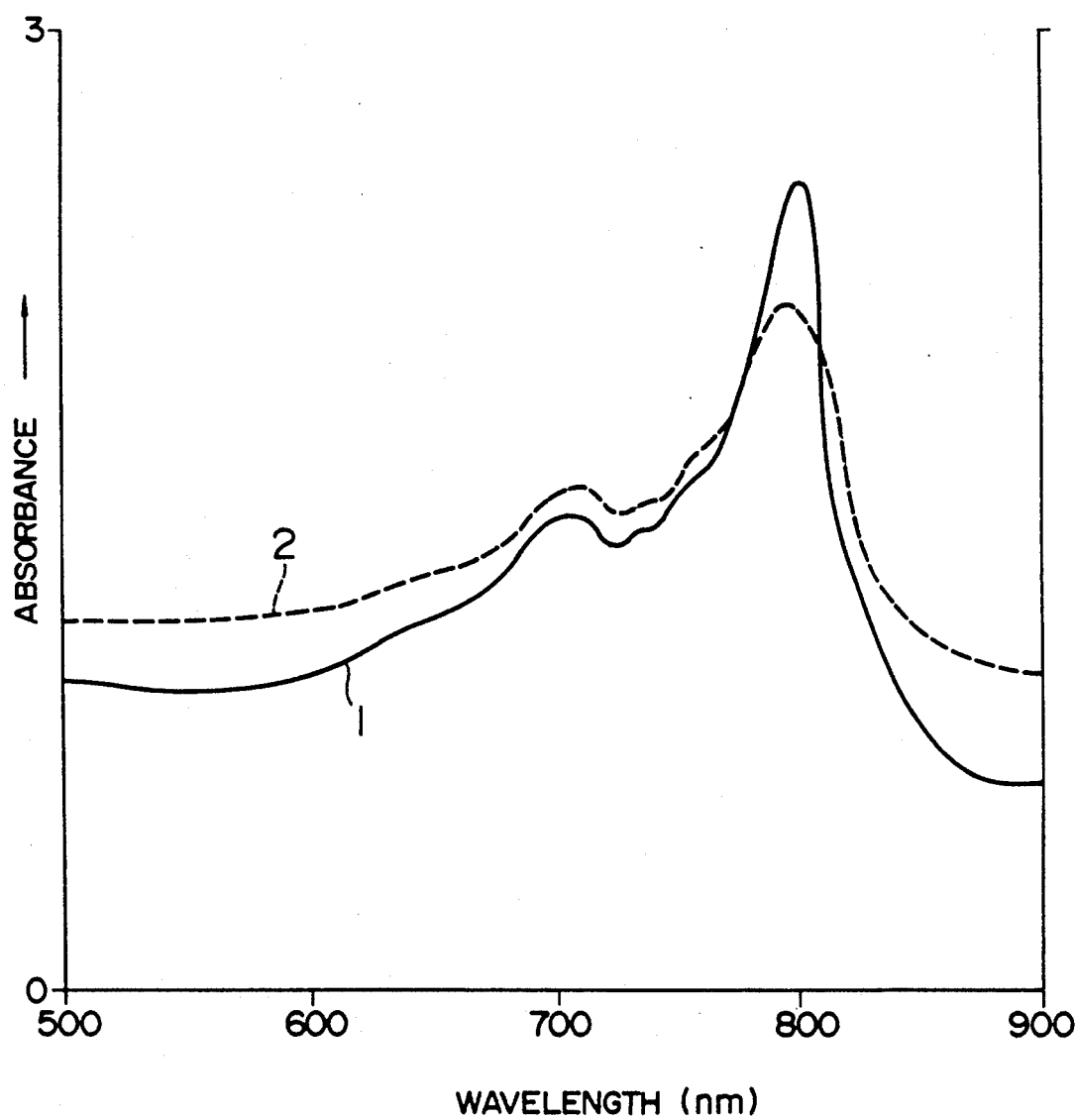
FIG. 1 is absorption spectrum of the recording medium of Example 1 using bis(trihexylsiloxy)-silicon naphthalocyanine as a recording material, wherein 1 is spectrum before irradiation of energy beam and 2 is spectrum after irradiation of energy beam.

The present invention relates to an optical recording medium having on a substrate a recording layer comprising an organic thin film containing a silicon naphthalocyanine compound represented by the following general formula (I):

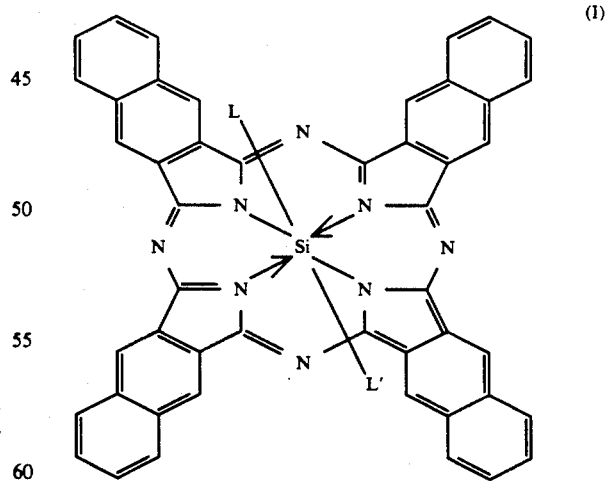

wherein L and L' each represents a group capable of linking to silicon.

In general formula (I), L and L' are appropriately selected from those groups which can form a covalent bond with the central metal silicon. Examples of the group usable as L and L' include alkyl group, alkoxy group, siloxy group represented by $R_1R_2R_3SiO-$ ($R_1$, $R_2$ and $R_3$ independently represent hydrogen atom, alkyl group or alkoxy group), hydroxyl group, halogen atom and the like.

When L and L' represent a group other than halogen and hydroxyl, the silicon naphthalocyanine compound used in the invention can be obtained, most generally, by reacting a silicon naphthalocyanine compound of general formula (I) wherein L and/or L' represent(s) a hydroxyl group with a compound corresponding to the group which can link to the central metal silicon. A concrete process for synthesizing the silicon naphthalocyanine compound of the invention will be mentioned below.

Thus, 1,3-diiminobenz(f)isoindoline and silicon tetrachloride are reacted at about 210° C. for about 2.5 hours, whereby a silicon haphthalocyanine compound of general formula (I) wherein L and L' each represents chlorine atom can be obtained. Subsequently, the latter is treated with acid and alkali, whereby the two chlorine atoms can be replaced with hydroxyl groups and there can be obtained a silicon naphthalocyanine compound of hydroxyl group. Subsequently, the latter is reacted with an alcohol or $R_1R_2R_3SiCl$ or $R_1R_2R_3SiOH$ at 140° C. to 150° C. for about 1.5 hours, whereby a silicon naphthalocyanine compound wherein L and L' represent alkoxy group or siloxy group can be obtained.

Silicon naphthalocyanine compounds of general formula (I) wherein one of L and L' represents alkyl group can be synthesized in the following manner. Thus, 1,3-diiminobenz(f)isoindoline and $RSiCl_3$ (R represents alkyl group) are reacted at about 210° C. for about 2.5 hours to obtain a silicon naphthalocyanine compound wherein one of L and L' represents chlorine atom and the other represents alkyl group. This compound may be used as the silicon naphthalocyanine compound of the invention. Otherwise, this compound is treated in the same manner as above, whereby a compound wherein the other of L and L' represents hydroxyl group, alkoxy group or siloxy group can be synthesized.

Silicon naphthalocyanine compounds of general formula (I) wherein L and L' each represents alkyl group can be obtained by reacting 1,3-diiminobenz(f)isoindoline and $R'R''SiCl_2$ (R' and R'' each represents alkyl group) at about 210° C. for about 2.5 hours.

Regarding L and L' in general formula (I), examples of the alkyl group include methyl, ethyl, propyl, butyl, hexyl and the like; examples of the alkoxy group include methoxy, ethoxy, propoxy, butoxy, pentoxy, hexoxy, heptoxy, octoxy, decoxy, dodecoxy, tetradecoxy, hexadecoxy, octadecoxy and the like; and, as the siloxy group represented by general formula $R_1R_2R_3SiO—$ ($R_1$, $R_2$ and $R_3$ independently represent hydrogen atom, alkyl group or alkoxy group), siloxy groups of general formula $R_1R_2R_3SiO—$ wherein the alkyl group referred to in the parenthesized proviso is methyl, ethyl, propyl, butyl, hexyl or the like and the alkoxy group is methoxy, ethoxy, propoxy, butoxy, pentoxy, hexoxy, heptoxy, octoxy, decoxy, dodecoxy, tetradecoxy, hexadecoxy, octadecoxy or the like can be referred to, and examples of such siloxy group include dimethylsiloxy, trimethylsiloxy, trimethoxysiloxy, dimethoxymethylsiloxy, dimethylpropylsiloxy, t-butyldimethylsiloxy, triethylsiloxy, triethoxysiloxy, tripropylsiloxy, tributoxysiloxy, dimethyloctylsiloxy, tributylsiloxy, trihexylsiloxy, and the like. From the viewpoint of recording characteristics, L and L' group represented by general formula $R_1R_2R_3SiO—$ ($R_1$, $R_2$ and $R_3$ independently represent hydrogen atom, alkyl group or alkoxy group). Most preferably, L and L' in general formula (I) independently represent a siloxy group represented by general formula $R_1R_2R_3SiO—$ wherein $R_1$, $R_2$ and $R_3$ independently represent an alkyl group having 1 to 4 carbon atoms.

The optical recording medium of the present invention is produced by providing a recording layer comprising a silicon naphthalocyanine compound represented by general formula (I) on an appropriate substrate.

When an amorphous layer of the silicon naphthalocyanine compound is provided on a substrate and it is spottily irradiated with a condensed electromagnetic energy having an appropriate intensity (e.g. diode laser beam), there occurs no perforation due to thermal deformation, but a crystallization occurs in the irradiated area after cooling it. This crystallization is accompanied by a change in optical density (reflectivity, absorptivity, or the like), which makes it possible to write informations into the layer. When the informations are to be read out, the layer is irradiated with an electromagnetic energy (e.g. diode laser) having such an intensity as to cause neither crystallization of the amorphous layer nor transformation of crystal into amorphous substance, and the optical densities of the silicon naphthalocyanine compound in the amorphous and crystalline areas are read out, whereby the informations can be read out.

Otherwise, the layer containing silicon naphthalocyanine compound provided on the substrate is irradiated with an electromagnetic energy (e.g. diode laser beam) having a high intensity to eliminate the silicon naphthalocyanine compound from the irradiated area and to induce a perforation there. By utilizing the change in optical density brought about by the perforation, informations can be written in and read out.

In forming the recording layer on a substrate, the silicon naphthalocyanine compound (optionally, together with a polymer such as polystyrene, nylon, polyvinyl butyral and the like) is dissolved or dispersed into an organic solvent such as methylene chloride, chloroform, 1,1,2-trichlorethane, toluene, benzene or the like, and the resulting solution or dispersion is formed into recording layer by the method of spin coating, dip coating, or the like. From the viewpoint of forming a recording layer having a uniform quality and obtaining good recording characteristics such as surface reflection, however, it is most preferable to form the recording layer by the vacuum vapor deposition method. As the method for forming an amorphous thin film, vacuum vapor deposition method is most preferable. In practising vacuum vapor deposition, temperature of the substrate is preferably lower than room temperature because such a temperature facilitates the formation of amorphous thin film, and the rate of vapor deposition should be as high as possible. The recording layer may be made from a single material or from combination or two or more materials. When two or more materials are used in combination, the structure of the layer may be a laminated structure or a single layer structure made of mixture of the materials. Thickness of the recording layer is preferably in the range of 50 to 10,000 Å and particularly in the range of 100 to 5,000 Å.

Although the material constituting the substrate of the recording medium is not critical, films or plates of inorganic materials such as glass, mica, metals, alloys and the like and organic high-polymeric materials such as polyester, cellulose acetate, nitrocellulose, polyethylene, polypropylene, polyvinyl chloride, vinylidenechloride copolymers, polyamide, polystyrene, polymethyl methacrylate, methyl methacrylate copolymers and the like are usually used. Bases made of an organic high polymer having a low heat conductivity are preferable from the viewpoint of minimizing the heat loss at the time of recording and enhancing the sensitivity.

The optical recording medium of the present invention may have an auxiliary layer such as metal layer, inorganic compound layer, organic high polymer layer and the like.

In optically regenerating the formed record image, reflected light is often used. In such as case, a metal layer is preferably provided on a recording layer surface of the opposite side of the substrate for the purpose of enhancing the contrast.

Further, in order to facilitate the amorphous-crystal transition in the recording layer and promoting the transformation into amorphous state at the time of forming the recording layer, it is preferable to provide a metal layer between the substrate and the recording layer. The metals used for this purpose include Al, Cr, Au, Pt, Sn and the like.

The metal layer can be formed according to the so far known thin film forming technics such as vacuum vapor deposition, sputtering plasma deposition and the like. Its film thickness may be selected in the range of 100 to 10,000 Å. For the purpose of improving the adhesive property of the metal layer, a layer of metal oxide mentioned layer may be provided under the metal layer.

When surface smoothness of substrate itself has an important meaning, a uniform film of organic high polymer may be provided on the substrate. For this purpose, commercially available polymers such as polyester, polyvinyl chloride and the like can be used.

In order to improving the stability of recording layer, a layer comprising inorganic compound may be provided on the upside surface, downside surface or both surfaces of recording layer. In order to promote the transition into amorphous state, a layer of inorganic compound may be provided on the downside surface of recording layer. As said inorganic compound, metal oxides such as PbO, $GeO_2$, $SiO_2$, $Al_2O_3$, $SnO_2$, SiO, $TiO_2$, $CeO_2$ and the like; metal sulfides such as PbS, ZnS, GeS, $Gr_2S_3$, CuS and the like; metal fluorides such as $MgF_2$, $CaF_2$, $CeF_2$ and the like; and metal nitrides such as TiN, $Si_3N_4$ and the like can be referred to. These layers have a thickness of about 50 to 1,000 Å. As the method for forming these layers, vacuum vapor deposition, sputtering, ion plating, plasma vapor deposition and the like can be used.

Preferably, a protective layer mainly composed of an organic high polymer is provided on the outermost layer to improve stability and protective property and to enhance sensitivity due to the decrease in surface reflectivity. Organic high polymers usable for this purpose include polyvinylidene chloride, polyvinyl chloride, vinylidene chloride-acrylonitrile copolymer, polyvinyl acetate, polyimide, polymethyl methacrylate, polystyrene, polyisoprene, polybutadiene, polyurethane, polyvinyl butyral, fluorinated rubber, polyester, epoxy resin, silicone resin, cellulose acetate and the like. These polymers may be used either alone or in the form of copolymer or blended product. Addition of silicone oil, antistatic agent, crosslinking agent and the like to these polymers is preferable from the viewpoint of improving the film performances. Further, two or more layers of organic high polymer may be used in a superposed state. The organic high polymer is dissolved into an appropriate solvent and then coated to form a layer. Otherwise, it is formed into a thin film and then laminated. Film thickness of such organic high polymer is 0.1 to 10 $\mu$m and preferably 0.1 to 2 $\mu$m.

WORKING EXAMPLES

Next, examples of the present invention will be mentioned. In the first place, production examples of the silicon naphthalocyanine compounds used in the examples will be mentioned.

PRODUCTION EXAMPLE 1

Production of Dihydroxysilicon naphthalocyanine

One hundred grams (0.67 mole) of sodium iodide was added to a well-stirred solution of 42.2 g (0.1 mole) of $\alpha,\alpha,\alpha',\alpha'$-tetrabromo-o-xylene and 13.5 g (0.173 mole) of fumaronitrile in 400 ml of anhydrous N,N-dimethylformamide, and the resulting mixture was stirred at 75° C. for about 7 hours in an atmosphere of nitrogen. After the reaction, the mixture was poured into about 2 kg of ice, and thereto was slowly added sodium hydrogen sulfite until the red-brown colored aqueous solution turned to light yellow. After adding a slightly excessive quantity of sodium hydrogen sulfite, the resulting mixture was stirred for a while and then allowed to stand overnight at room temperature. The deposited light yellow-colored solid product was collected by filtration with suction, thoroughly washed with water, and allowed to dry. The light yellow-colored solid product thus obtained was recrystallized from ethanol/chloroform mixture to obtain 13 g (73%) of 2,3-dicyanonaphthalene as a colorless crystalline material.

It had a melting point of 256.5°–257.5° C. (256° C. in literature).

Next, in an atmosphere of nitrogen, 0.64 g (28 mmoles) of metallic sodium was added in five portions to 90 ml of anhydrous methanol to prepare a methanolic solution of sodium methoxide. To the methanolic solution was added 10.2 g (57.3 mmoles) of 2,3-dicyanonaphthalene. While thoroughly stirring the mixture, anhydrous ammonia gas was bubbled into the mixture slowly over a period of about one hour at room temperature. Then, the mixture was heated under reflux for about 3 hours while bubbling anhydrous ammonia gas. After cooling the mixture, the deposited yellow-colored solid product was collected by filtration, thoroughly washed with methanol and dried in vacuum. Thus, about 9.5 g (86%) of 1,3-diiminobenzo(f)isoindoline was obtained as a yellow colored solid. It was used in the subsequent reaction without purification.

In an atmosphere of nitrogen, 20 ml of anhydrous tri-n-butylamine was added to 6 g (30.6 mmoles) of 1,3-diiminobenzo(f)isoindoline suspended in 40 ml of anhydrous tetraline. Then, 5.4 ml (47.1 mmoles) of silicon tetrachloride was added, and the resulting mixture was heated under reflux for about 3 hours. After cooling it, 30 ml of methanol was added, and the resulting mixture was allowed to stand overnight. The red-brown colored reaction mixture was filtered and the filter cake was thoroughly washed with methanol and dried under reduced pressure. Thus, about 4 g (64%) of dichlorosilicon naphthalocyanine was obtained as a deep green colored solid product. It was used in the subsequent reaction without purification.

To 200 ml of concentrated sulfuric acid was added 5.8 g (7.15 mmoles) of dichlorosilicon naphthalocyanine. The mixture was stirred for about 2 hours. The reaction mixture was poured into about 600 g of ice, and allowed to stand overnight. The resulting precipitate was collected by filtration and washed three times with water and then three times with acetone/water (1:1) mixture. Then, the precipitate was heated under reflux in 150 ml of concentrated aqueous ammonia for about one hour. After cooling it, it was collected by filtration, thoroughly washed with water and dried under reduced pressure. Thus, about 4 g (72%) of dihydroxysilicon naphthalocyanine was obtained as a deep green colored solid product.

PRODUCTION EXAMPLE 2

Production of Bis(triethylsiloxy)-silicon naphthalocyanine

To 774 mg (1 mmole) of dihydroxy-naphthalocyanine suspended in 35 ml of quinoline was added 3.5 ml (23 mmoles) of triethylsilanol. The mixture was heated under reflux for about 3 hours. After cooling the reaction mixture, it was poured into 200 ml of ethanol/water (1:1) mixture. The resulting mixture was thoroughly stirred and allowed to stand overnight. The resulting precipitate was collected by filtration and washed with methanol. Soluble fraction of this precipitate was dissolved out with about 600 ml of hot chloroform, and the resulting chloroform solution was concentrated to a volume of about 50 ml. The concentrated chloroform solution was cooled, and the resulting crystalline precipitate was collected by filtration and washed with chloroform. The crystal thus obtained was recrystallized from chloroform to obtain 360 mg (36%) of deep green colored crystalline product. Based on the analyses mentioned below, it was identified as bis(triethylsiloxy)-silicon naphthalocyanine, i.e. a compound of general formula (I) wherein $L = -O-Si-(-C_2H_5)_3$.

(1) Melting point: >300° C.
(2) Elementary analyses:

|  | C | H | N |
|---|---|---|---|
| Calculated (%) | 71.82 | 5.42 | 11.17 |
| Found (%) | 70.45 | 5.34 | 10.92 |

(3) NMR: in CDCl$_3$ solvent
δ:
10.13(8H, s)
8.68(8H, dd, J=6.10, 3.05 Hz)
7.93(8H, dd, J=6.10, 3.05 Hz)
−1.02(12H, t, J=7.93 Hz)
−2.07(18H, q, J=7.93 Hz)

PRODUCTION EXAMPLE 3

Production of Bis(tri-n-butylsiloxy)-silicon naphthalocyanine

In an atmosphere of nitrogen, 12 ml (50.4 mmoles) of anhydrous tri-n-butylamine and then 13.2 ml (49.2 mmoles) of tri-n-butylchlorosilane were added to a suspension of 3 g (3.9 mmoles) of dihydroxysilicon naphthalocyanine in 420 ml of anhydrous 8-picoline. The mixture was heated under reflux for about 2 hours. After cooling the mixture, it was poured into 600 ml of ethanol/water (1/1) mixture, thoroughly stirred and allowed to stand overnight. The resulting precipitate was collected by filtration and washed with water. Its soluble fraction was dissolved out with about 600 ml of hot chloroform, and the chloroform solution was dried on anhydrous sodium sulfate and concentrated to about 50 ml. The concentrated crystalline precipitate was collected by filtration and washed with chloroform. The mother liquor was concentrated, passed through a chromatographic alumina column and eluted by using benzene as a eluent. The eluted green-colored benzene solution was concentrated and treated with n-hexane. The resulting crystalline precipitate was collected by filtration and thoroughly washed with hexane All the crude crystals thus obtained were united and recrystallized from chloroform to obtain about 2 g (44%) of deep green colored crystal. Based on the analyses mentioned below, it was identified as bis(tri-n-butylsiloxy)silicon naphthalocyanine.

(1) Melting point: >300° C.
(2) Elementary analyses:

|  | C | H | N |
|---|---|---|---|
| Calculated (%) | 73.81 | 6.71 | 9.50 |
| Found (%) | 73.71 | 6.73 | 9.40 |

(3) NMR: CDCl$_3$
δ:
10.11(8H, s)
8.67(8H, dd, J=6.10, 3.35 Hz)
7.92(8H, dd, J=6.10, 3.35 Hz)
−0.1∼0.1(30H, m)
−0.97(12H, quintet, J=7.32 Hz)
−2.07(12H, t, J=7.32 Hz)

PRODUCTION EXAMPLE 4

Production of Bis(tri-n-propylsiloxy)-silicon naphthalocyanine

Anhydrous tri-n-butylamine (12 ml, 50.4 mmoles) and then 10.8 ml (49.2 mmoles) of tri-n-propylchlorosilane were added to a suspension of 3 g (3.9 mmoles) of dihydroxysilicon naphthalocyanine in 420 ml of anhydrous β-picoline. The mixture was heated under reflux for about 2 hours. After cooling the mixture, it was treated in the same manner as in Production Example 3 and recrystallized from chloroform to obtain 1.45 g (34%) of a deep green colored crystalline product. Based on the analyses mentioned below, it was identified as bis(-tri-n-propylsiloxy)-silicon naphthalocyanine.

(1) Melting point: >300° C.
(2) Elementary analyses:

|  | C | H | N |
|---|---|---|---|
| Calculated (%) | 72.89 | 6.12 | 10.30 |
| Found (%) | 72.70 | 6.13 | 10.28 |

(3) NMR: CDCl$_3$
δ:
10.03(8H, s)
8.68(8H, dd, J=6.10, 3.03 Hz)
7.93(8H, dd, J=6.10, 3.03 Hz)
−0.28(18H, t, J=7.32 Hz)
−0.85(12H, sextet J-7.32 Hz)
−2.06(12H, t, J=7.32 Hz)

PRODUCTION EXAMPLE 5

Production of Bis(tri-n-hexylsiloxy)-silicon naphthalocyanine

Anhydrous tri-n-butylamine (4 ml, 16.8 mmoles) and then 6 ml (16.4 mmoles) of tri-n-hexylchlorosilane were added to a suspension of 1 g (1.3 mmoles) of dihydroxysilicon naphthalocyanine in 140 ml of anhydrous 8-picoline. The mixture was heated under reflux for 1.5 hours. After cooling the mixture, insoluble impurities were filtered off, and the filtrate was poured into 200 ml of ethanol/water (1/1) mixture. The resulting precipitate was collected by filtration, thoroughly washed with water and dried in vacuum. The product thus obtained was passed through a chromatographic alumina column and eluted with toluene-hexane mixture (3:1) as a eluent. The deep green colored solution thus obtained was concentrated and the concentrate was recrystallized from hexane/chloroform to obtain 0.52 g (30%) of a green-colored needle-like crystal. By comparing the analyses mentioned below with literature, this compound was identified as bis(tri-n-hexylsiloxy)-silicon naphthalocyanine.

(1) Melting point: 277°–278° C. (Literature value: 278° C.)

(2) NMR: CDCl$_3$ $\delta$:

10.11(8H, s)

8.67(8H, dd, J=6.21, 3.35 Hz)

7.91(8H, dd, J=6.21, 3.35 Hz)

0.63(12H, sextet, J=7.32 Hz)

0.42(18H, t, J=7.32 Hz)

0.23(12H, quintet, J=7.32 Hz)

0.07(12H, quintet, J=7.32 Hz)

−0.98(12H, quintet, J=7.32 Hz)

−2.06(12H, t, J=7.32 Hz)

EXAMPLE 1

On a polymethyl methacrylate plate having a thickness of 5 mm, a layer of silicon oxide was formed by vacuum vapor deposition up to a thickness of 150 Å, and then aluminum was vacuum vapor deposited up to a thickness of 150 Å. Further thereon was formed a layer of bis(trihexylsiloxy)-silicon naphthalocyanine up to a thickness of 2,000 Å by the method of vacuum vapor deposition (substrate temperature: room temperature; boat temperature: 350° C.; degree of vacuum: $4\times10^{-6}$ Torr). Further thereon was formed a layer of silicon oxide just in the same manner as above up to a thickness of 150 Å. The recording material thus obtained was irradiated with xenon flash lamp (manufactured by Miyata Denki Co., model MXQF-1125; condenser capacity: 2,200 $\mu$F, pulse width: 60 $\mu$sec) to make a record as a change in optical density. The minimum charging voltage of xenon flash lamp required for the recording was measured, from which discharging energy of the lamp (($\frac{1}{2}$)CV$^2$; wherein C is capacity of condenser and V is charging voltage) was determined. Using this value, sensitivity of the recording material was evaluated. As the result, its sensitivity was found to be 7.5 Joules.

FIG. 1 illustrates the light absorption spectra before and after irradiation of energy light. In FIG. 1, solid line 1 indicates the property before irradiation, while dotted line 2 indicates the property after irradiation. By utilizing this difference in optical density, the record can be read out by the use of, for example, laser beam.

EXAMPLE 2

On a polymethyl methacrylate plate having a thickness of 5 mm, a layer of silicon oxide and a layer of aluminum were formed just in the same manner as in Example 1. Subsequently, a layer of bis(tributylsiloxy)-silicon naphthalocyanine was formed up to a thickness of 1,500 Å by vacuum vapor deposition method (substrate temperature: room temperature; boat temperature: 380° C.; degree of vacuum $4\times10^{-6}$ Torr). Further thereon, a layer of silicon oxide were formed in the same manner as in Example 1. Sensitivity of the recording material thus obtained was evaluated in the same manner as in Example 1. As the result, its sensitivity was found to be 8.0 Joules.

EXAMPLE 3

A recording layer was prepared just in the same manner as in Example 2, except that bis(tripropylsiloxy)-silicon naphthalocyanine was used as the recording material. The layer of bis(tripropylsiloxy)-silicon naphthalocyanine was formed by vacuum vapor deposition method (substrate temperature: room temperature; boat temperature: 410° C.; degree of vacuum: $4\times10^{-6}$ Torr) so that thickness of the layer came to 1,500 Å. Sensitivity of the recording medium thus obtained, which evaluated in the same manner as in Example 1, was 8.6 Joules.

EXAMPLE 4

A recording layer was formed just in the same manner as in Example 2, except that bis(triethylsiloxy)-silicon naphthalocyanine was used as the recording material. The layer of bis(triethylsiloxy)-silicon naphthalocyanine was formed by vacuum vapor deposition method (base degree of vacuum: $4\times10^{-6}$ Torr) so that thickness of the layer came to 1,500 Å. Sensitivity evaluated in the same manner as in Example 1 was 9.4 Joules.

COMPARATIVE EXAMPLE 1

On a polymethyl methacrylate plate having a thickness of 5 mm, a layer of silicon oxide having a thickness of 100 Å was formed by vacuum vapor deposition method. Thereon was formed a layer of metallic bismuth (an inorganic recording material) by vacuum vapor deposition method up to a thickness of 500 Å. Further thereon was formed a layer of silicon oxide in the same manner as above up to a thickness of 100 Å. Sensitivity of this recording material evaluated in the same manner as in Example 1 was 28 Joules.

Concretely, informations can be written into and read out of the recording media of the invention (those mentioned in Examples) in the following manner.

Thus, a diode laser beam of 8 mW is condensed to a spot diameter of 1~2 $\mu$m, and it is irradiated onto the recording medium to make a record. In reading out the recorded informations, a He—Ne laser beam of 0.5 mW (oscillation wavelength 633 nm) is irradiated onto the recording medium and the difference in optical density of reflecting beam is measured.

With the silicon naphthalocyanine compounds of the examples of the present invention, informations could be written in and read out by the above-mentioned procedure. With the recording medium of the comparative example using bismuth as recording material, however, informations could not be written-in completely.

EXAMPLE 5

Figure 6:
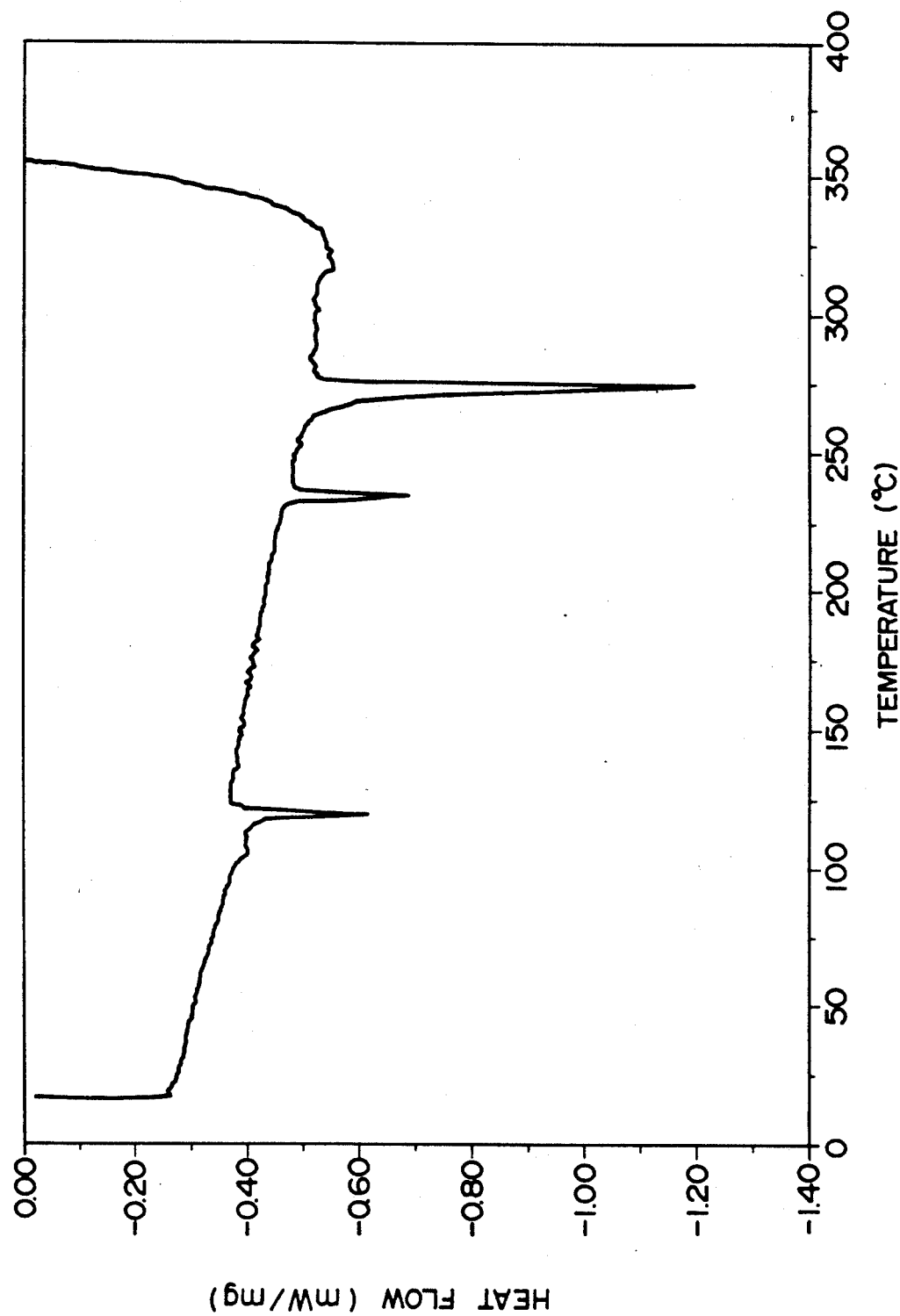
FIGS. 6 through 9 are graphs illustrating the results of differential scanning calolimetric measurement (DSC) of He-NC, Bu-NC, Pr-NC and Et-NC, respectively in the mentioned order.
Figure 10:
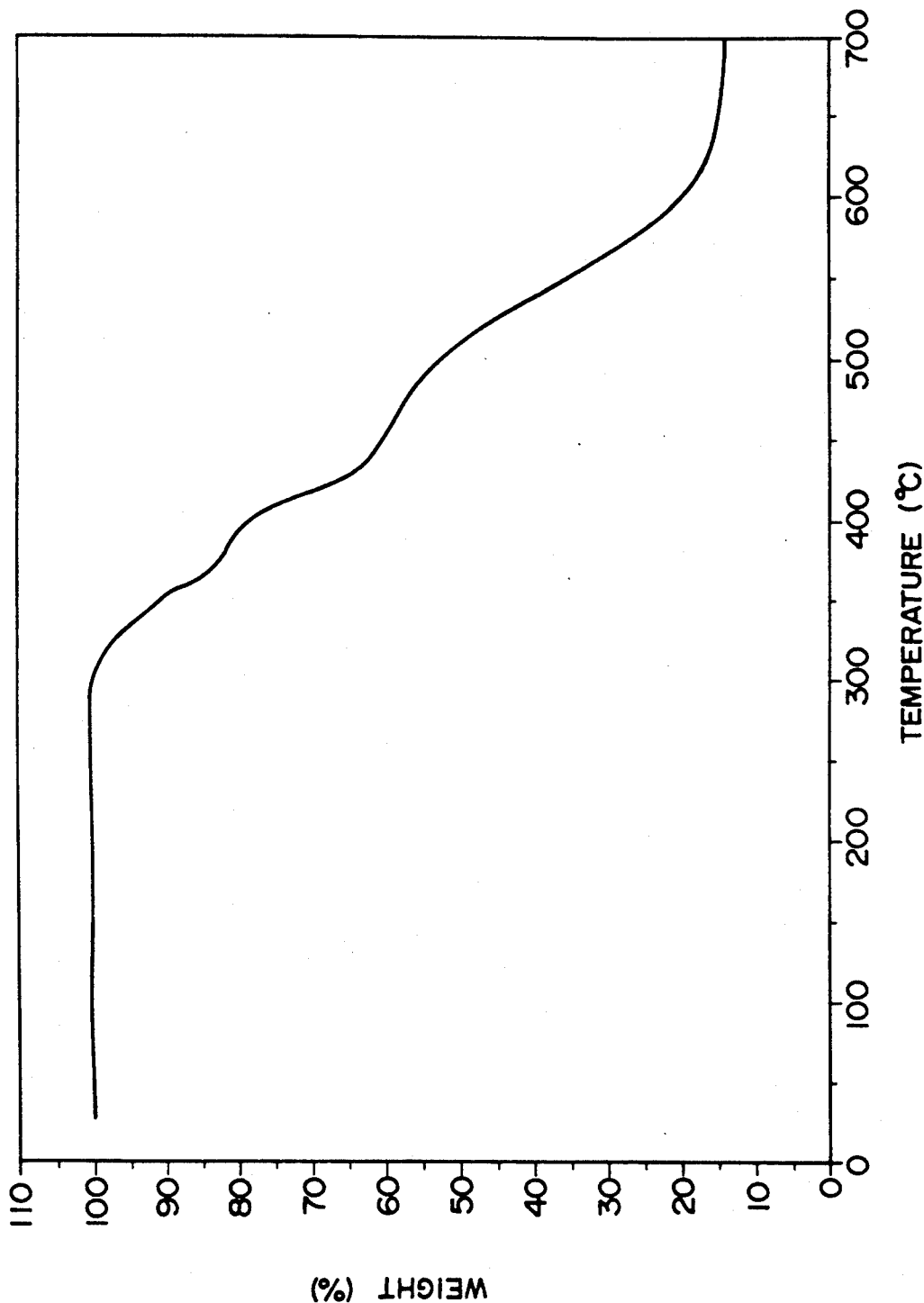
FIGS. 10 through 13 are graphs illustrating the results of thermogravimetric analysis (TGA) of He-NC, Bu-NC, Pr-NC and Et-NC, respectively in the mentioned order.

On a glass plate having a thickness of 1.2 mm, a layer of bis(trihexylsiloxy)-silicon naphthalocyanine (hereinafter, simply referred to as He-NC) having a thickness of 500 Å was formed by vacuum vapor deposition method (substrate temperature: room temperature; boat temperature: 350° C.; degree of vacuum: $8 \times 10^{-6}$ Torr) The recording material thus obtained was irradiated with a 5 mW diode laser (oscillation wavelength 830 nm) having a condensed beam diameter of 1.6 μm at a beam velocity of 0.5 m/sec through the glass plate to make a record. The sectional shape of the record pits in the irradiated area was measured by means of an electron microscope equipped with sectional shape measuring apparatus (manufactured by Elionics Co.). FIG. 2 illustrates the sectional shape. Differential scanning calorimatric measurement (DSC) of He-NC was carried out with Thermal Analyzer 9900 (manufactured by Du Pont) (sample weight: 2.5 mg; temperature rising speed: 5° C./min.). The results are shown in FIG. 6. Further, thermogravimetric analysis (TGA) of He-NC was caried out with the same apparatus as above. The results are shown in FIG. 10. The starting temperature of loss in weight upon heating and the velocity of loss in weight upon heating determined from FIG. 10 are shown in Table 1. Further, melting point of He-NC was measured with Yanagimoto Micro Melting Point Apparatus MP-S3 (manufactured by Yanagimoto Seisakusho) (sample weight 0.1 mg; temperature rising speed: 2° C./min.; temperature range: 20°-300° C.). The results are shown in Table 2.

EXAMPLES 6 THROUGH 8

Figure 11:
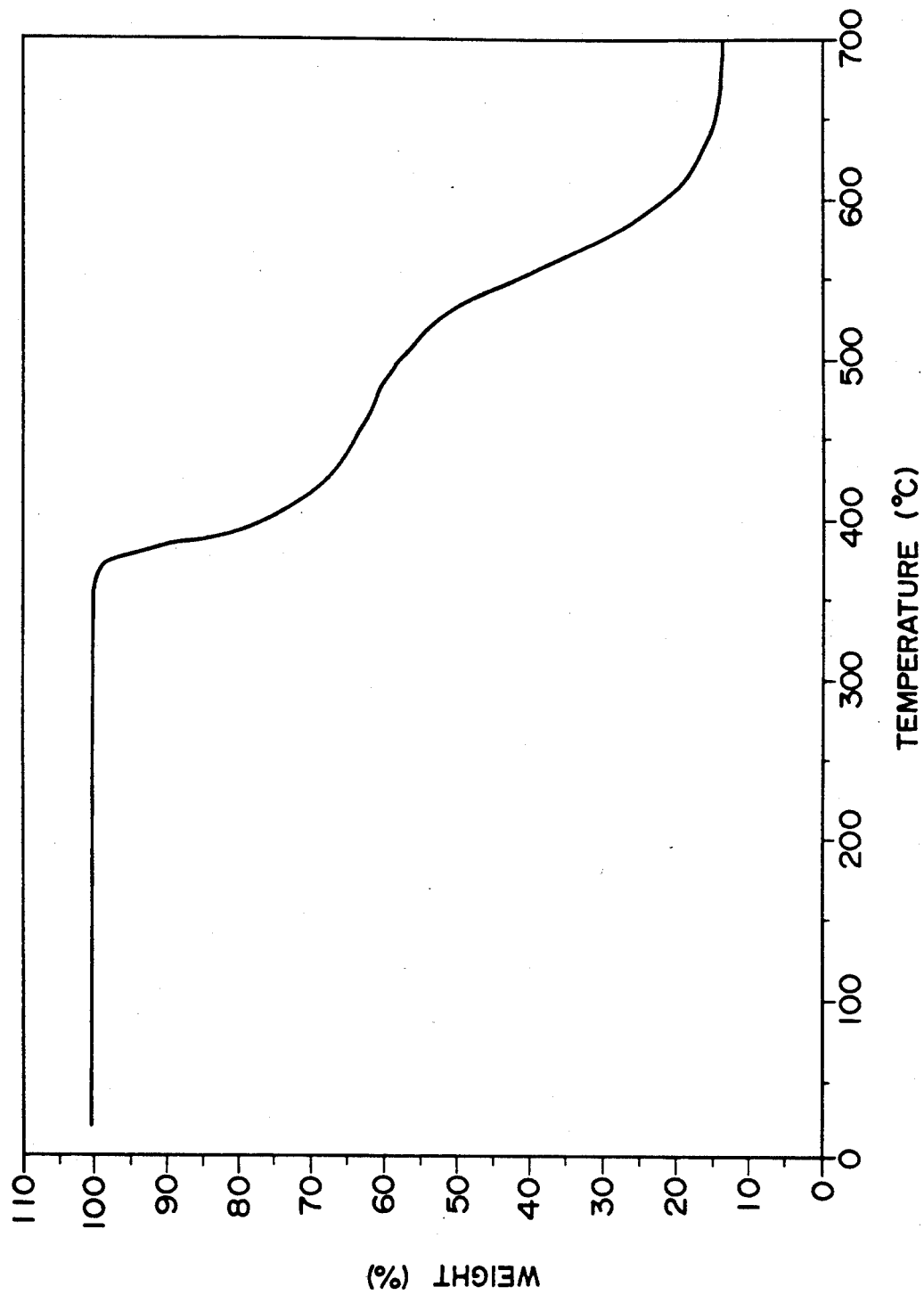
Figure 12:
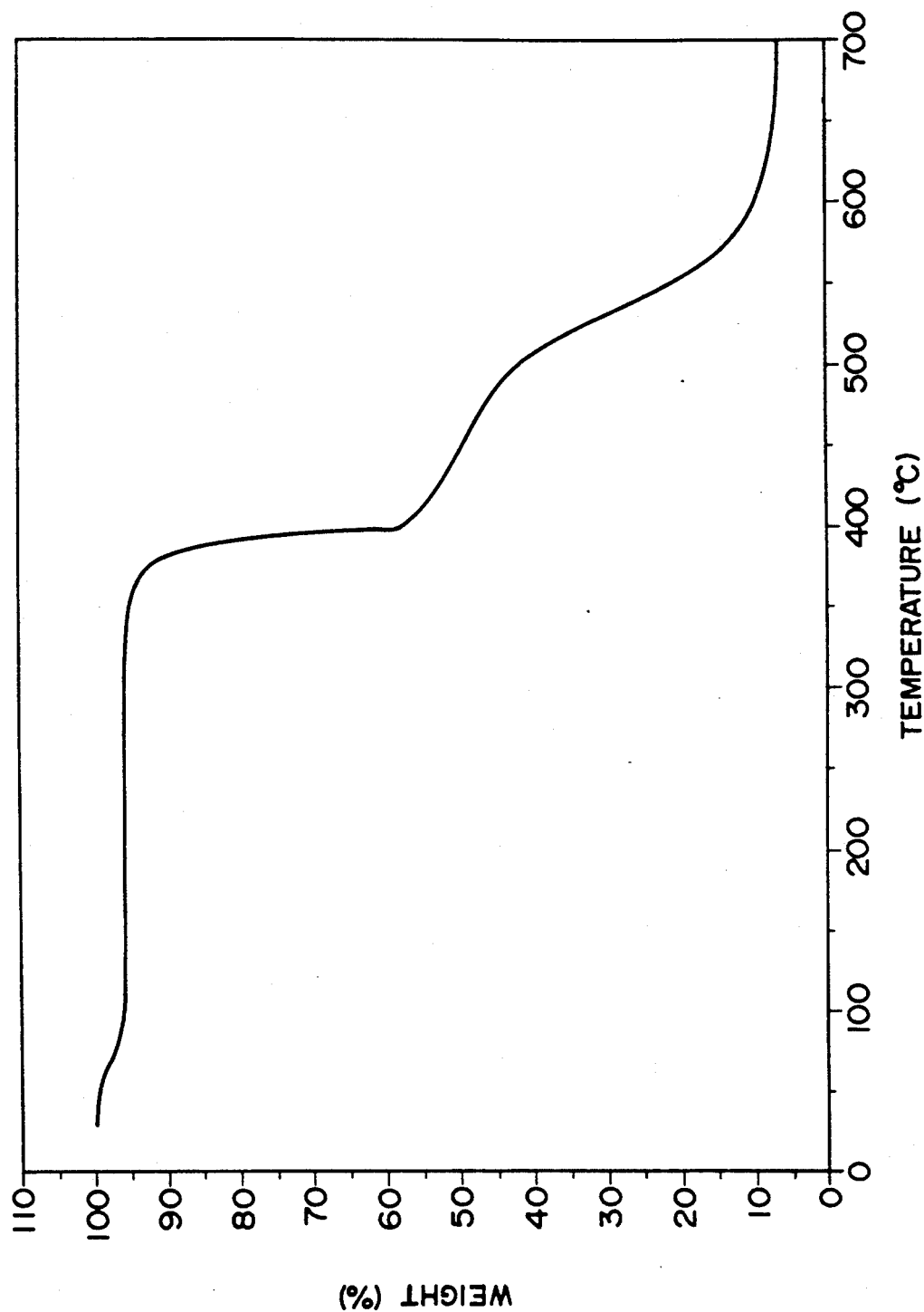
Figure 13:
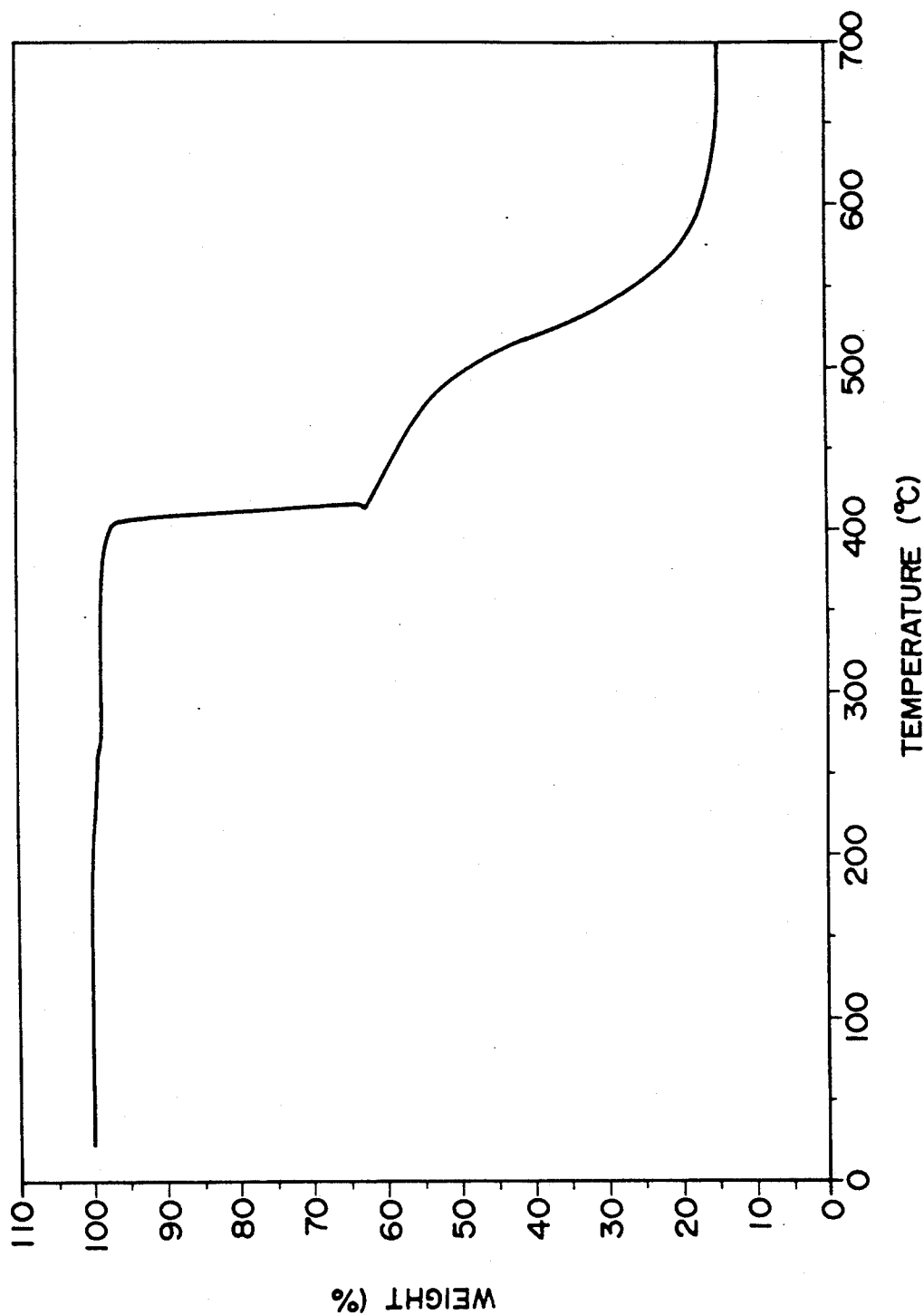
Figure 14:
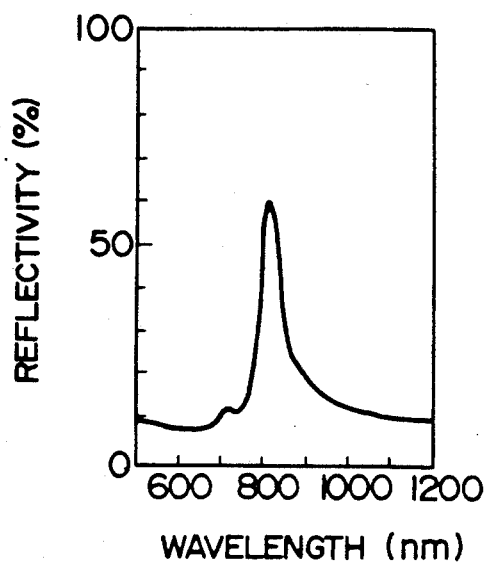
FIGS. 14 through 17 are reflection spectra of the recording materials using He-NC, Bu-NC, Pr-NC and Et-NC of Examples 5 through 8, respectively in the mentioned order.
Figure 15:
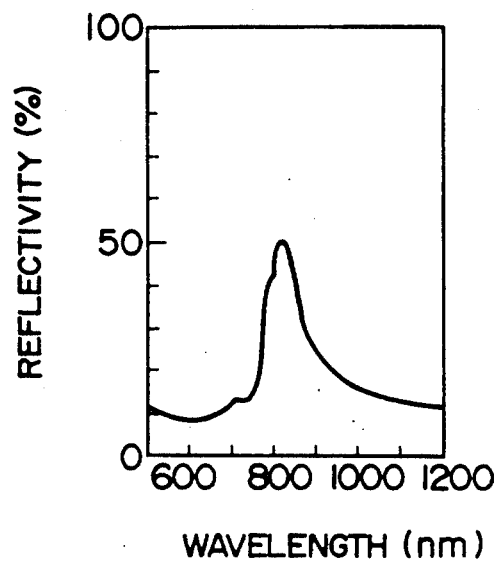
Figure 16:
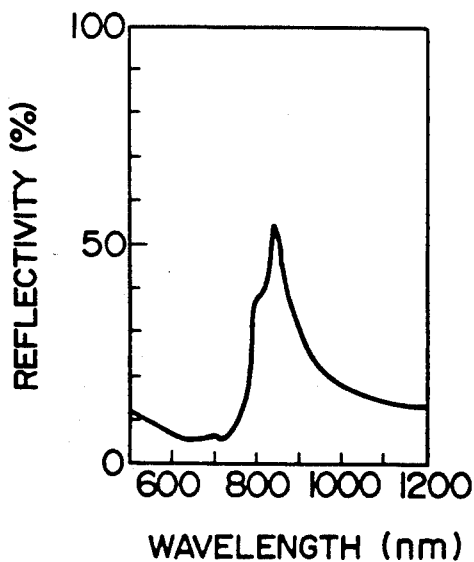
Figure 17:
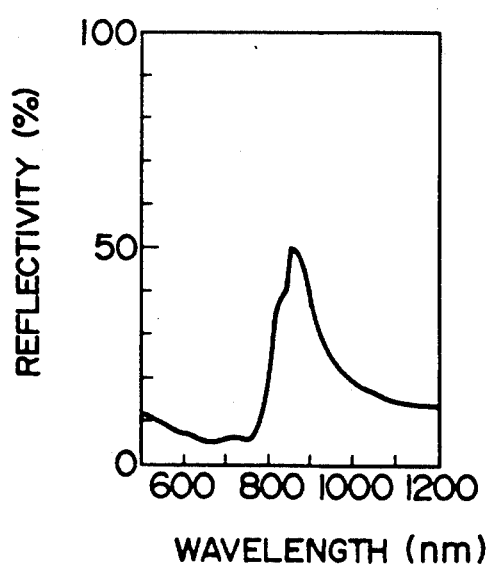

Recording materials were prepared from bis(tributylsiloxy)-silicon naphthalocyanine (hereinafter, simply referred to as Bu-NC) (Example 6), bis(tripropylsiloxy)-silicon naphthalocyanine (hereinafter, simply referred to as Pr-NC) (Example 7) and bis(triethylsiloxy)silicon naphthalocyanine (hereinafter, simply referred to as Et-NC) (Example 8) in the same manner as in He-NC, except that the boat temperature at the time of vacuum vapor deposition in the preparation of recording material was 380° C., 410° C. and 460° C., respectively (in the mentioned order). Further, sectional shape, DSC, TGA and melting point were measured in the same manner as in He-NC. The results are shown in FIGS. 3, 4 and 5 (sectional shapes of Bu-NC, Pr-NC and Et-NC), FIGS. 7, 8 and 9 (DSC of Bu-NC, Pr-NC and Et-NC), FIGS. 11, 12 and 13 (TGA of Bu-NC, Pr-NC and Et-NC), Table 1 (starting temperature of loss in weight upon heating, velocity of loss in weight upon heating), and Table 2 (melting point).

TABLE 1

| Name of sample | Starting temperature of loss in weight upon heating (°C.) | Velocity of loss in weight upon heating (%/min.) |
| --- | --- | --- |
| He-NC | 300 | 1.4 |
| Bu-NC | 363 | 2.2 |
| Pr-NC | 367 | 5.8 |
| Et-NC | 400 | 10.3 |

TABLE 2

| Name of sample | Melting point (°C.) |
| --- | --- |
| He-NC | 275 |
| Bu-NC | Not observed |
| Pr-NC | Not observed |
| Et-NC | Not observed |

Figure 7:
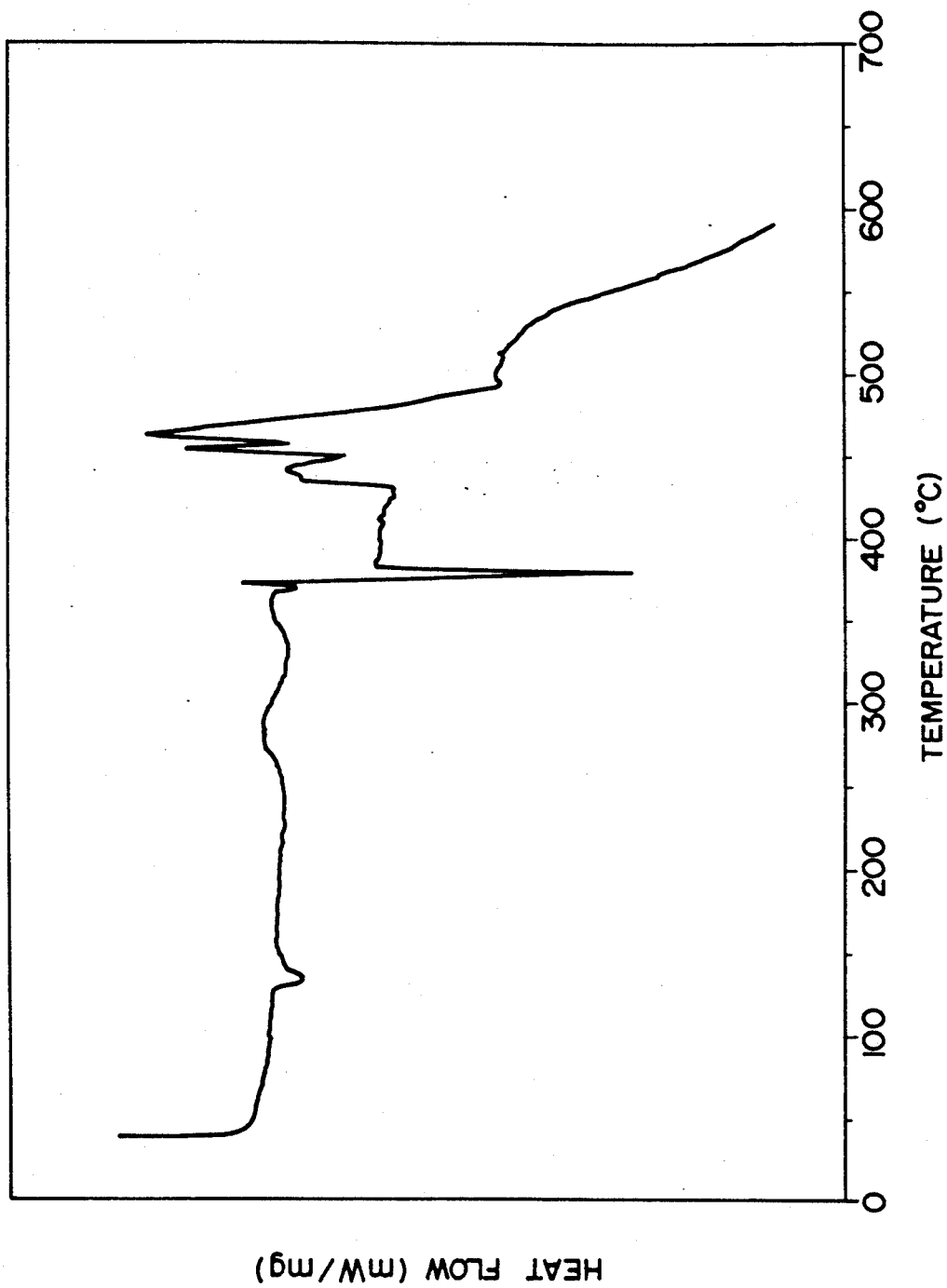
Figure 8:
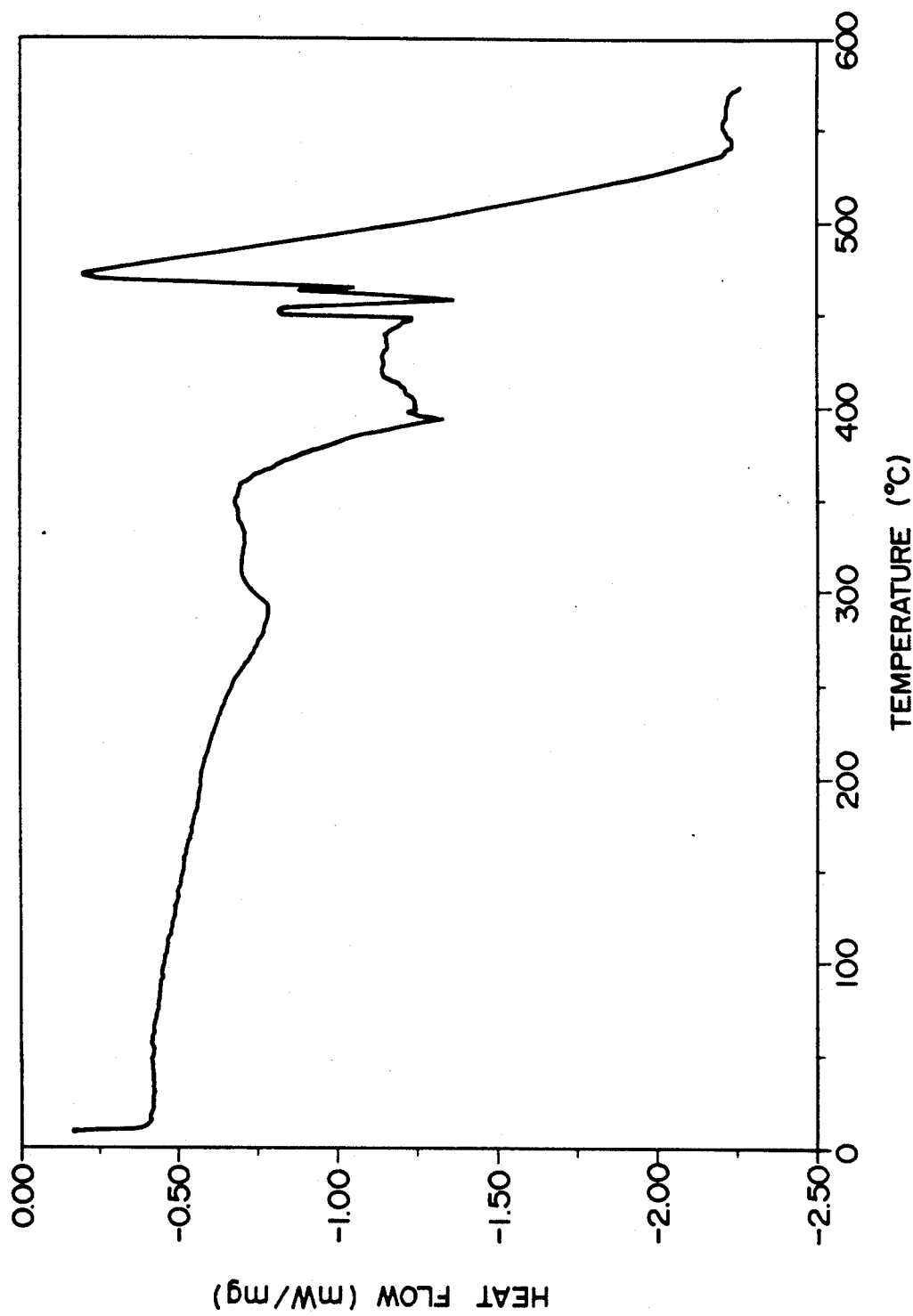
Figure 9:
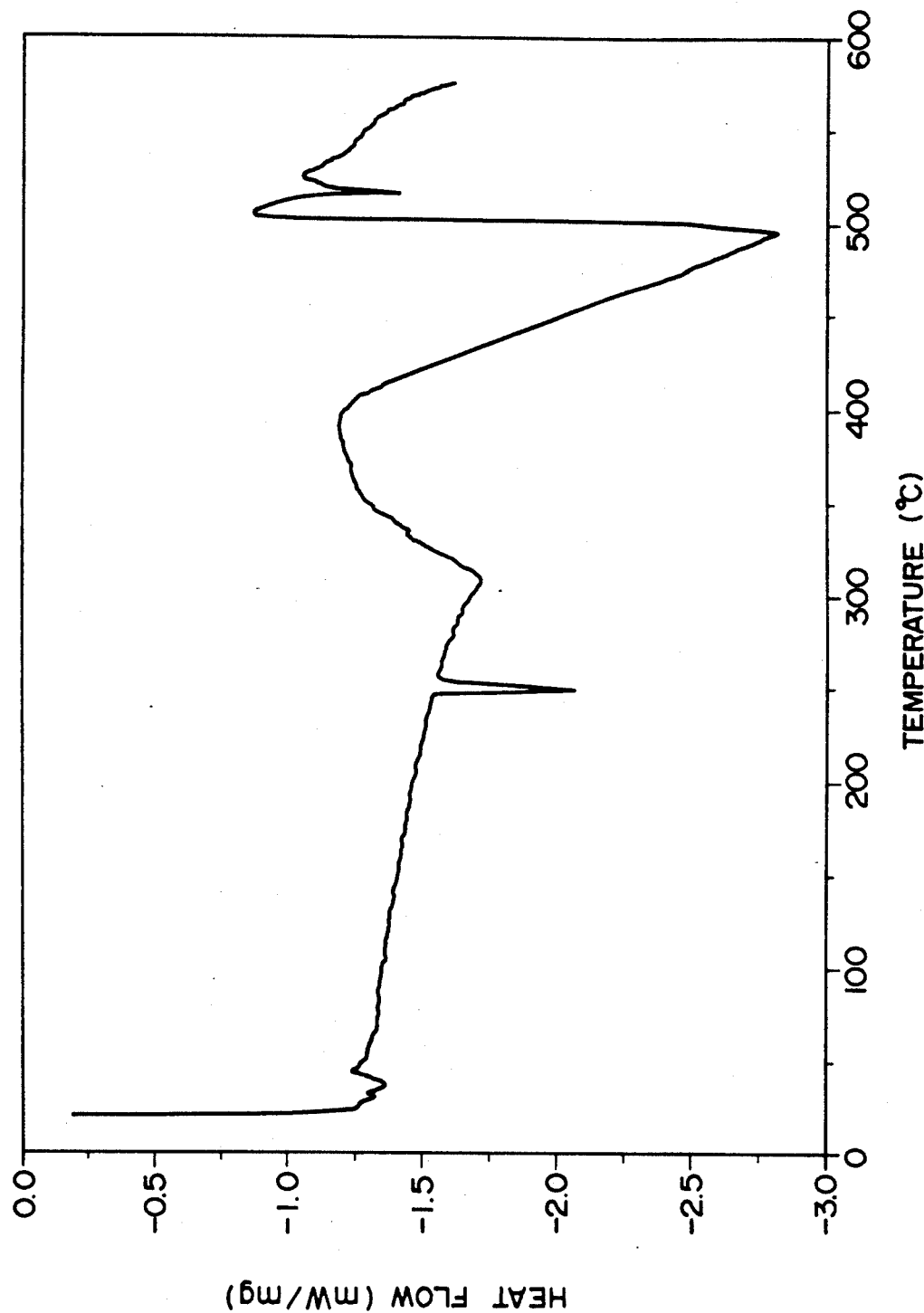

It is apparent from FIGS. 2 through 5 (sectional shapes) that He-NC exhibits a remarkable protrusion called "rim", while Et-NC hardly exhibits rim and Bu-NC exhibits a slight rim which is not so remarkable as in He-NC. FIGS. 6 through 8 (DSC) and Table 2 (melting point) demonstrate that He-NC shows a clear melting point at about 275° C., while Bu-NC, Pr-NC and Et-NC show no clear melting point up to 370°-400° C. (starting temperature of loss in weight upon heating, Table 1). The velocity of loss in weight upon heating (Table 1) demonstrates that the velocity of loss in weight upon heating decreases in order to Et-NC, Pr-NC, Bu-NC, He-NC. Taking the velocity of loss in weight upon heating of He-NC as unity, those of Bu-NC, Pr-NC and Et-NC are about 1.5, about 4 and about 7, respectively. A higher velocity of loss in weight upon heating suggests a higher efficiency of heat utilization at the time of pit formation.

Based on the above-mentioned results, it is understandable that the contribution of thermal fusion decreases in order to He-NC, Bu-NC, Pr-NC, Et-NC and the contribution of thermal decomposition decreases in the reverse order. That is to say, pit is formed mainly due to thermal fusion in case of He-NC, while pit is formed mainly due to thermal decomposition in case of Et-NC.

As for the shape of pit, Et-NC is most excellent, and it is followed by Pr-NC, Bu-NC and He-NC in the mentioned order. That it to say, a pit formation to which thermal decomposition contributes to a greater extent gives a sharper threshold characteristic of recording sensitivity and forms a more regularly shaped pit without strain so that a recording material allowing such a pit formation is more desirable than a material allowing a pit formation to which thermal fusion contributes to a greater extent.

FIGS. 14 through 17 illustrate reflection spectra of the recording materials obtained in Examples 5 through 8 measured by means of Automatic Recording Spectrophotometer model 330 manufactured by HITACHI. The reflection spectrum of He-NC (FIG. 14) is sharp, while those of Pr-NC, Bu-NC, and He-NC (FIGS. 15, 16 and 17) are broad. The latter three materials are superior to He-NC in adaptability to diode laser (oscillation wavelength 780 nm or 830 nm).

EXAMPLE 9

On a glass plate having a thickness of 1.2 mm, a solution prepared by dissolving 5 mg of He-NC into 1 g of chloroform was spin-coated by means of a spinner (model 1H-2 manufactured by Mikasa Co.) at a rotation speed of 2,000 rpm to form a layer of said compound having a thickness of 50 nm (recording layer coated film).

Figure 18:
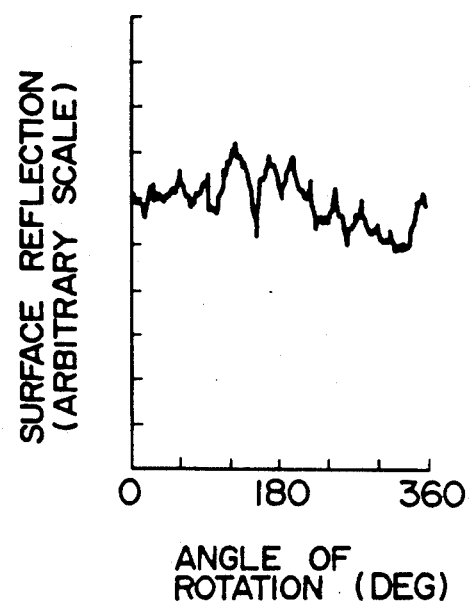
FIG. 18 is a chart illustrating the surface reflection of a recording material prepared by dissolving He-NC into a solvent, coating it and drying it.
Figure 19:
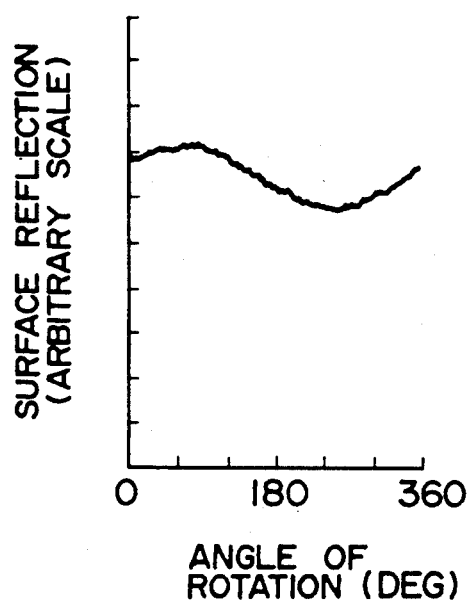
FIG. 19 is a chart illustrating the surface reflection of a recording material prepared by vapor depositing He-NC of Example 5.

Surface reflectivity of the recording layer coated film thus obtained and surface reflectivity of the recording material obtained in Example 5 (recording layer vapor deposited film) were studied by irradiating them with 0.5 mW laser beam while rotating the bases and detecting the reflected beam with photoelectron amplifier. The results are shown in FIG. 18 (recording layer coated film) and FIG. 19 (recording layer vapor deposited film).

Even though the recording layer vapor deposited film shows some long-range undulations in surface reflection, the local unevenness of surface reflection is smaller than the recording layer coated film, demonstrating that vapor deposited film is more uniform in quality than coated film. Further, by irradiating a semiconductor laser beam with a wavelength of 830 nm on these recording layer coated film and recording layer vapor deposited film from the side of glass plate, recording characteristics were evaluated. Consequently, a record could be made respectively under a 5.2 mW and 4.4 mW semiconductor laser having a beam diameter of 1.6 μm at a beam velocity of 0.5 m/sec.

EFFECT OF THE INVENTION

Owing to the use of specified silicon naphthalocyanine compound as the material of recording layer, the optical recording medium of the present invention shows a high sensitivity characteristic and enables to use laser beams as an effective electromagnetic energy for writing-in and reading-out.

What is claimed is:

1. A vapor deposited optical recording medium of a pyrolytic type having on a substrate a recording layer on which information can be recorded to form pits and read directly afterwards by means of a laser providing light of a predetermined frequency, said information is the relative reflection between the recording layer in which pits have not been formed and these areas in which pits have been formed in the recordation of information, said recording layer comprising an organic thin film containing a silicon naphthalocyanine compound represented by the following general formula (I):

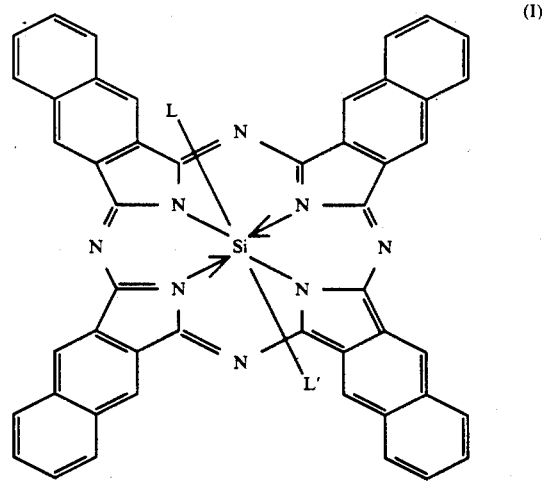

wherein L and L' independently represent a siloxy group represented by general formula $R_1R_2R_3SiO-$; $R_1$, $R_2$ and $R_3$ independently representing an alkyl group having 1 to 3 carbon atoms.

2. An optical recording medium according to claim 1, wherein said silicon naphthalocyanine compound is selected from the group consisting of bis(tripropylsiloxy)-silicon naphthalocyanine and bis(triethylsiloxy)-silicon naphthalocyanine.

* * * * *